United States Patent [19]

Walker et al.

[11] 4,107,439
[45] Aug. 15, 1978

[54] PROCESS FOR PREPARING ARYLALKANOIC ACID DERIVATIVES

[75] Inventors: Jerry A. Walker, Osthemo Township, Kalamazoo County; David R. White; William G. Salmond, both of Kalamazoo, all of Mich.

[73] Assignee: The Upjohn Company, Kalamazoo, Mich.

[21] Appl. No.: 696,720

[22] Filed: Jun. 16, 1976

[51] Int. Cl.$^2$ .................. C07C 69/76; C07C 65/00; C07C 63/52

[52] U.S. Cl. .................................. 560/55; 560/56; 560/100; 560/102; 560/105; 260/515 R; 260/592; 260/448.2 P; 260/612 D; 260/613 B; 260/520 R; 260/520 D

[58] Field of Search ............... 260/473 R, 476 R, 469, 260/448.2 B, 515 R, 520 R, 520 D

[56] References Cited

PUBLICATIONS

McKillop, A. et al., JACS 95, pp. 3340–3343, 1973.

Primary Examiner—Paul J. Killos
Attorney, Agent, or Firm—John T. Reynolds

[57] ABSTRACT

2-Aryl-$C_3$ to $C_6$-alkanoate esters are prepared economically by reacting an enol ether of an aryl alkyl ketone with a trivalent thallium salt in an organic solvent. The ester intermediate product is then converted to the corresponding 2-aryl-$C_3$ to $C_6$-alkanoic acid or salt thereof. The aryl group is selected so the resulting acid product will be a useful compound such as an anti-inflammatory, analgesic and anti-pyretic drug or agriculturally useful product. Examples of drug acids which can be made by this process include ibuprofen, flurbiprofen, fenoprofen and naproxen and the like.

18 Claims, No Drawings

PROCESS FOR PREPARING ARYLALKANOIC ACID DERIVATIVES

INTRODUCTION

This invention relates to chemical processes for preparing 2-arylalkanoic acid compounds. More particularly, this invention provides an improved process for preparing useful 2-aryl-$C_3$ to $C_6$-alkanoate, and preferably 2-arylpropionate esters, and the resulting acids and salts thereof. This invention is particularly concerned with providing an improved process for preparing 2-aryl-$C_3$ to $C_6$-alkanoic acid compounds which are useful as antiinflammatory, analgesic and anti-pyretic drug compounds.

BACKGROUND OF THE INVENTION (a) 2-Arylalkanoic acids

A variety of 2-arylalkanoic acids are now known to be useful as active anti-inflammatory, analgesic and anti-pyretic pharmaceutical drug products. A few of the better known include the 2-arylpropionic acid derivatives such as fenoprofen which is 2-(3-phenoxyphenyl)-propionic acid and related compounds which are described in Marshall U.S. Pat. No. 3,600,437, ibuprofen which is 2-(4-isobutylphenyl)propionic acid and which is described with other related compounds in Nicholson et al. U.S. Pat. No. 3,385,886, naproxen which is 2-(6-methoxy-2-naphthyl)propionic acid which is described with other related compounds in Belgian Pat. No. 747,812 (Derwent Index No. 71729R-B). In addition a large variety of other 2-aryl-$C_3$ to $C_6$-alkanoic acid compounds are described in the medical, pharmaceutical and patent literature including the above patent references as well as Shen U.S. Pat. No. 3,624,142, and Adams et al. U.S. Pat. No. 3,793,457 which patents describe some fluoro-substituted biphenylalkanoic acids. Another compound of interest of this latter type is flurbiprofen which is 2-(2-fluoro-4-biphenylyl)propionic acid. Thus, a large variety of 2-aryl-$C_3$ to $C_6$-alkanoic acids, and particularly the 2-arylpropionic acid drug compounds are known and more of such compounds will undoubtedly be discovered and described in the future patent and other technical literature.

(b) Prior Processes

The above patent references also describe a variety of process routes for preparing useful 2-aryl-$C_2$ to $C_6$-alkanoic acids. However, some of the prior processes suffer a variety of disadvantages including expensive starting materials, dangerous by-products, and gross quantities of by-products necessitating substantial expense in destroying or getting rid of such by-products. As a result chemists skilled in chemical process research continue to study and search for improved processes for making the more economically significant 2-aryl-$C_3$ to $C_6$-alkanoic acids, and particularly the 2-arylpropionic acids.

Among the possible process routes being explored to prepare the useful ester compounds are processes involving the use of trivalent thallium salts as reactants. A. McKillop et al. in the *Journal of the American Chemical Society* (JACS), 95 (1973) pp. 3340–3343 describe a process for preparing methyl arylacetates by the oxidative rearrangement of acetophenones with thallium (III) nitrate (TTN). Treatment of acetophenone at room temperature with 1 equivalent of TTN in a mixture of methanol and 70% aqueous perchloric acid (5 to 1) resulted in smooth reduction of the TTN to thallium (I) nitrate; precipitation of the inorganic salt was complete after 5 hours. Filtration and evaporation of the filtrate gave an oil which by glpc analysis, consisted of two components in the ratio of 16:1. They were identified as methyl phenylacetate (94%) and ω-methoxyacetophenone (6%). Distillation of the mixture gave pure methyl phenylacetate in 84 percent yield. When this process was applied to the oxidation of propiophenone with TTN in acidic methanol a mixture of products was obtained, which consisted of methyl α-methylphenyl acetate (45%) and α-methoxypropiophenone (32%).

See also *Chemical Abstracts*, 82, (1975) page 501, item 16821x (abstracting Japan Kokai 74 48661) which refers to the production of 2-substituted benzothiazolacetic acid esters using perchloric acid-methanol mixtures. However, chemists and engineers concerned with designing large scale chemical processes would prefer to avoid process conditions which would involve the use of perchloric acid-methanol mixtures which are potentially hazardous or explosive. E. C. Taylor and A. McKillop also disclosed a process for preparing methyl 2-phenylpropionate as the only substantial product by reacting propiophenone with anhydrous trivalent thallium trinitrate on a Florisil support at the April, 1974 American Chemical Society (ACS) meeting in Los Angeles and the IUPAC meeting in Belgium in August, 1974, respectively. However, as is apparent from the above reports, working directly with the ketone reactant (here the propiophenone) and trivalent thallium salt in an aqueous organic medium results in a yield lowering mixture of products which chemical process chemists and engineers would prefer to avoid. Also, when the ketone is reacted directly with the anhydrous trivalent thallium salt on a Florisil support (TTN: Florsil = 1:2 w/w) a large quantity of the inert Florisil is required because the trivalent thallium salt supported thereon reacts mole for mole (stoichiometric proportions) with the ketone reactant. The reaction in commercial scale operation would thus produce huge quantities of monovalent thallium salt on Florisil support which must be handled or otherwise disposed of, thus inherently increasing the total cost of the process. Those skilled in the chemical process art continue to search for improved, technically practical, economical processes for preparing these valuable drug compounds, which would avoid the above problems.

OBJECTS OF THE INVENTION

It is an object of this invention to provide an improved process for preparing 2-aryl-substituted $C_3$ to $C_6$-alkanoate esters, and the acids therefrom, based upon the use of trivalent thallium salts, which process minimizes the production of undesired yield-lowering byproducts and potential hazards and eliminates the necessity for using inert, solid support materials for the thallium salt reactant to obtain substantially only the desired 2-arylalkanoate ester intermediate product.

It is a further object of this invention to provide an improved process for preparing 2-aryl-substituted $C_3$ to $C_6$-alkanoate esters which are useful as intermediates for preparing the corresponding 2-aryl-$C_3$ to $C_6$-alkanoic acids which are useful as the active ingredient in anti-inflammatory, analgesic and anti-pyretic pharmaceutical formulations, either per se or as a pharmaceutically acceptable salt thereof.

It is a more specific object of this invention to provide an improved process for preparing some particular 2-arylpropionate esters which are useful as intermediates for preparing the corresponding 2-arylpropionic acids which have anti-inflammatory, analgesic and antipyretic properties in a potency sufficient to make them of interest as commercial drug products.

Other objects, aspects and advantages of this invention will be apparent to one skilled in this art from the description and claims which follow.

SUMMARY OF THE INVENTION

Briefly, according to this invention it has been found that 2-aryl-substituted $C_3$ to $C_6$-alkanoate esters can be prepared in high yields as substantially the only organic product by reacting an enol ether derivative of an aryl $C_2$ to $C_5$-alkyl ketone with a trivalent thallium salt in an organic liquid medium containing at least one equivalent of an alcohol, water or other nucleophile. If the enol ether is generated in situ from the ketal or ketone the organic solvent system should be substantially anhydrous. If the trivalent thallium salt used in processes where the enol ether is to be generated in situ is hydrated, a water scavenger compound such as a trialkyl ortho ester, should be included in the reaction mixture for best yields. When the enol ether derivative is used directly as substrate the solvent medium may contain some water, and hydrated forms of the trivalent thallium salt can be used (although anhydrous forms of the thallium salt also work well). The aryl group on the ketone, ketal, or enol ether starting material is selected to provide the resulting 2-aryl-$C_3$ to $C_6$-alkanoic acid product with useful properties, such as anti-inflammatory, analgesic and anti-pyretic drug properties or herbicidal, plant growth regulatory or other practically useful properties. The substituent on oxygen of the ketal or enol ether can be any group which will form a 2-aryl-$C_3$ to $C_6$-alkanoate ester and which ester group is easily removed by known procedures to form the corresponding 2-aryl-$C_3$ to $C_6$-alkanoic acid products. The process of this invention produces substantially only the 2-aryl-$C_3$ to $C_6$-alkanoate ester, thus bringing the practical yields closer to the theoretical yields, while avoiding the necessity for including any bulky, inert support materials for the thallium compound in the reaction mixture and also the necessity of acid catalysis.

DETAILED DESCRIPTION OF THE INVENTION

More specifically, this invention provides a process for preparing 2-aryl-$C_3$ to $C_6$-alkanoate esters which comprises reacting an enol ether of the formula

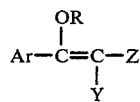
(III)

with trivalent thallium ions in an organic liquid medium containing at least one equivalent of an alcohol or water at a temperature of from about −25° C. to about reflux temperature of the mixture for a time sufficient to form the 2-aryl-$C_3$ to $C_6$-alkanoate ester product

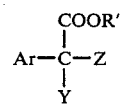
(I)

wherein Ar is the aromatic moiety of a useful acid product, containing from 6 to 13 carbon atoms, in which the aryl ring portion of the aromatic moiety is a phenyl, phenoxyphenyl, naphthyl or biphenylyl group bonded to the carbon atom adjacent to the carbonyl carbon atom (of the carboxylate ester product) at an aryl ring carbon; R in III above is $C_1$ to $C_4$-alkyl, benzyl, phenyl, tris ($C_1$ to $C_3$-alkyl)silyl or the like; R' is equal to R or is $C_1$ to $C_4$-alkyl, phenyl, or benzyl group derived from the solvent medium; and Y and Z denote the residue of the $C_3$ to $C_6$-alkyl moiety and each of Y and Z can be hydrogen or $C_1$ to $C_4$-alkyl, with Y and Z having a total of from one to 4 carbon atoms.

We prefer to prepare the enol ether reactant in situ from a readily available ketone of the formula

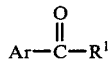

wherein Ar is as defined above and $R^1$ is $-(CH_2)_n-H$ where $n$ is 2 to 5 or $-CH(Y)Z$ wherein Y and Z are as defined above, through a ketal intermediate of the formula

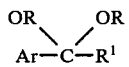
(II)

wherein Ar, R and $R^1$ are as defined above, under substantially anhydrous, acidic conditions.

The enol ether to ester reaction should be conducted in an organic liquid diluent which contains an equivalent amount of alcohol, preferably a $C_1$ to $C_6$-alkanol, or water or another nucleophilic compound relative to the enol ether content in the mixture. The organic liquid diluent itself can be the preferred alcohol but it can also be an aprotic liquid. The lower alkanol or water are the preferred simplest and most economical examples of the oxygen nucleophile which is needed to promote the reaction. The nucleophile can be an oxygen containing compound having the capability of reacting with an electrophile by bond formation through the oxygen atom. Examples of other oxygen nucleophiles which can be present in the reaction mixture for this purpose include alkanoic acids, e.g., acetic, propionic, butyric, benzoic acids and alkali metal salts thereof and the like. When efforts are being made to maintain anhydrous conditions substances such as tri($C_1$ to $C_3$-alkyl)ortho $C_1$ to $C_4$-carboxylic esters or tetra ($C_1$ to $C_3$-alkyl)orthosilicates should be included in the reaction mixture. The process will operate at pH conditions below 7 but it works best when the reaction medium is on the more acidic side of pH 5.

This process can be used as part of an overall process to prepare a wide variety of useful aryl-$C_3$ to $C_6$-alkanoic acids. Acid products of immediate concern to us are those which have medicinal uses when compounded into appropriate pharmaceutical formulations and dosage forms. Examples of such compounds which can be made from this process include those wherein Ar is 3-phenoxyphenyl, $C_3$ to $C_5$-alkylphenyl, 4-biphenylyl, 4-biphenylyl substituted with up to 3 fluorine atoms on ring carbons thereof and 2-naphthyl substituted in the 6-position thereof with methoxy. Also, 2-phenyl $C_3$ to $C_6$-alkanoic acids such as 2-phenylpropionic acid, and 2-methyl-2-phenylpropionic acid and the like which have plant growth regulatory properties can also be prepared by the process of this invention.

Enol ether compounds (III) are sometimes formed as a mixture of stereoisomers, but the success of the process does not depend upon the isomer configuration or isomer ratio of the enol ether, so the stereoconfigurations are not shown here, and such mixtures of enol ethers can be used in this process.

The trivalent thallium ions are obtained from trivalent thallium salts. These salts should be a salt which will ionize under the reactant mol ratio, solvent and temperature reaction conditions to create an electrophilic thallium ion species in the mixture. Examples of the more practical readily ionizable thallium salts for this process include the trivalent thallium nitrate, sulfate, bisulfate, perchlorate, fluoroborate, orthrophosphate and chloride and bromide salts. However, the trivalent thallium halide such as trivalent thallium chloride and bromide appear to require substantially anhydrous conditions to be of practical value in this process. Organic acid salts of $C_1$ to $C_6$-alkanoic and $\alpha$-haloalkanoic acids such as trivalent thallium acetate, propionate, isobutyrate, hexanoate, $\alpha$-chloroacetate, $\alpha$-bromoacetate, $\alpha$-chloropropionate, $\alpha$-bromopropionate, $\alpha$-chlorobutyrate, and the $\alpha$-dichloro and trichloroacetates as well as thallium benzoate and $C_1$ to $C_6$-alkanesulfonic acid salts such as methane sulfonate, hexanesulfonate and $C_6$ to $C_{10}$-arylsulfonate salts such as benzenesulfonate, p-toluenesulfonate salts of trivalent thallium can also be used.

The reaction of the process of this invention occurs between the enol ether and the trivalent thallium ions in the mixture. When the enol ether is used directly as substrate with the more highly electrophilic thallium salts such as TTN, it is not critical or necessary to maintain rigorously anhydrous conditions. The presence of water from hydrated thallium salts or adventitious water introduced with the organic solvent systems does not seriously impair this process, but where water is present it is in some cases desirable to maintain the reaction mixture at a somewhat higher pH, say pH of 3 to 5 by the addition of a base such as sodium hydroxide. We have found that where this process is to be conducted starting from the selected ketone or the ketal it is desirable, to take reasonable measures to insure substantially anhydrous conditions in the mixture. Likewise when trivalent thallium halide salts such as the chloride or bromide are used, substantially anhydrous conditions are necessary to insure the presence of sufficiently electrophilic trivalent thallium ions in the reaction mixture.

We have also found that this process can be operated starting directly from the selected ketone or ketal to generate the enol ether reactant in situ by contacting the ketone with an alcohol and water scavenger in an anhydrous medium and in the presence of acid to drive the equilibrium of the mixture toward reaction from the ketone to the ketal to the enol ether. The presence of water in this ketone and ketal mixture is detrimental to this desired reaction route so that reasonable care should be taken to avoid the presence of water in these ketone and ketal containing reaction mixtures. While avoiding the presence of water one can add the trivalent thallium salt to the reaction mixture which will react with the enol ether in the mixture to form the 2-aryl-$C_3$ to $C_6$-alkanoate ester product (I).

Once the enol ether is formed any trivalent thallium salt which will ionize to form an electrophilic trivalent thallium ion in the reaction mixture can be used. However, when the process is to be conducted in one reaction vessel starting from the ketone or ketal, the presence of a strong acid i.e., an acid having a pKa of less than about 4 is required to drive the reaction toward the formation of the enol ether in the mixture. If a trivalent thallium salt derived from a weak acid, that is the conjugate acid of the anion has a pKa greater than about 4 is to be used, the mixture will require the addition of a strong acid to catalyze the formation of the enol ether in the mixture.

Although the reactions of the process of this invention will proceed to at least some extent at low temperatures, as low as about $-25°$ C, and the reactants and products are stable enough to withstand reflux temperatures of the reaction mixtures at atmospheric pressure, experience indicates that with the preferred more highly electrophilic thallium salts such as trivalent thallium nitrate or sulfate and enol ether reactants, temperature ranges of from about $-10°$ to about $50°$ C. are sufficient and preferred. When a ketone or ketal is used as substrate, reaction temperatures of from about $30°$ C. to about $80°$ C. appear bet to complete the reactions in a reasonable period of time, say, 1 to 10 hours. With some combination of reactants and solvents it may be desirable to conduct the reaction at elevated pressures to push the reactions to completion in shorter periods of time, but for most combinations of reactants atmospheric pressure is sufficient to complete the reaction in 1 to 10 hours.

The preferred ketone, ketal, and enol ether starting materials are those having an aryl (Ar) group, which is common to useful drug acids and include, for example 3-phenoxyphenyl, $C_3$ to $C_5$-alkylphenyl, 4-biphenylyl, 4-biphenylyl substituted with a total of up to about 3 fluorine atoms in the phenyl ring thereof, and 2-naphthyl substituted in the 6-position with methoxy and R is $C_1$ to $C_4$-alkyl, and $R^1$ is $C_2$ to $C_4$-alkyl. Useful compounds can also be made by the process of this invention where the aryl group is a simple unsubstituted phenyl, naphthyl or biphenylyl.

Ketones which can be used to prepare the ketal and enol ether starting materials for use in the process of this invention are known compounds or can be prepared by procedures known in the art. Examples include those of the formula

(IV)

wherein Ar denotes the aryl moiety in known arylalkanoic acid compounds, and includes those Ar groups described, for example, in Marshall U.S. Pat. No. 3,745,223, Marshall U.S. Pat. No. 3,600,437, the biphenylyl and substituted biphenylyl groups described in Shen U.S. Pat. No. 3,624,142, the fluoro-4-biphenylyl groups described in Adams et al. U.S. Pat. Nos. 3,793,457 and 3,755,427, 2-fluoro-4-biphenylyl, the 3,4-(disubstituted phenyl) groups described in Krausz et al. U.S. Pat. No. 3,876,800, and the 4-substituted phenyl groups described, for example, in Nicholson et al. U.S. Pat. No. 3,228,831 and the 6-substituted 2-naphthyl groups in Belgian Pat. No. 747,812, and $R^1$ is

or

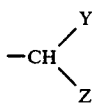

wherein n is 2 to 5, Y and Z are $C_1$ to $C_4$-alkyl or hydrogen with at least one of Y and Z being $C_1$ to $C_4$-alkyl. A preferred subgroup of ketones for use in preparing the ketals and enol ethers for use in the process of this invention are the aryl ethyl ketones, wherein the Ar group is as exemplified above. The most preferred ketones would be those which possess the Ar moieties which are of established economic interest for use in preparing the most useful and commercialized acid compounds e.g., useful drug acid compounds. Examples of these ketones would be those ketones wherein Ar in the above formula IV is 4-isobutylphenyl, 4-phenoxyphenyl, 3-phenoxyphenyl, 2-fluoro-4-biphenylyl, 6-methoxynaphthyl, and $R^1$ is $—(CH_2)_nH$ wherein n is 2 to 4.

Procedures for making the ketal (acetal) and enol ether starting materials from the ketones for the process of this invention are known in the art. Examples of such procedures include:

(A) reaction of the selected ketone with a trialkyl orthoester such as trimethyl orthoformate in the presence of an acid catalyst such as sulfuric acid, methanolic hydrogen chloride, p-toluenesulfonic acid, ferric chloride or ammonium nitrate, styrene-divinylbenzene copolymer sulfonic acid resin materials such as those sold under tradenames or trademarks such as Amberlyst-15 (see "Amberlyst-15, a Superior Catalyst for the Preparation of Enol Ethers and Acetals" by S. A. Patwardhan et al. in SYNTHESIS, May, 1974, pp. 348–349).

(B) reaction of the ketone with siple alcohols, preferably $C_1$ to $C_4$-alkanols, in the presence of an acid catalyst, including the use of sulfonic acid exchange resins such as the styrene/divinylbenzene copolymer sulfonic acid resins exemplified by Amberlyst-15 (Rohm & Haas Company, Philadelphia) and Dowex 50 (Dow Chemical Company, Midland, Michigan) at low temperature, e.g., $-28°$ C., favors the formation of the ketone acetal (see *J. of Organic Chemistry*, Vol. 24, November, 1959 pp. 1731–1733, an article by N. B. Lorette et al., entitled "Preparation of Ketone Acetals from Linear Ketones and Alcohols").

(C) reaction of the selected ketone with acetone dimethyl acetal (2,2-dimethoxypropane) to effect transketalization, as described in an article entitled "Preparation of Ketals from 2,2-Dimethoxypropane" by N. B. Lorette et al. in J. Org. Chem., Vol. 25, April, 1960, pp. 521–525.

(D) conversion of the corresponding ketal (acetal) to the enol ether by distillation over catalysts such as p-toluenesulfonic acid (see SYNTHESIS, supra).

For the preparation of the preferred aryl alkyl ketones a Friedel-Crafts reaction can be used, e.g., to effect reaction according to the following general format

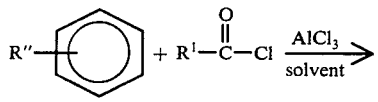

-continued

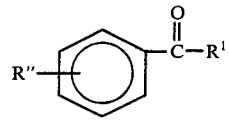

wherein R" is the residue of the desired aryl (Ar) group and $R^1$ is the residue of the carboxylic acyl halide. For example, the 6-methoxy-2-naphthyl propiophenone can be prepared by reacting 6-methoxynaphthalene with propionyl chloride in the presence of aluminum chloride in methylene chloride. The resulting 6-methoxy-2-naphthyl ethyl ketone is converted to the ketal starting material for this process by reacting it with trimethyl orthoformate in the presence of acid. The 3-phenoxyphenyl ethyl ketone ketal can be prepared by reacting 3-hydroxyphenyl ethyl ketone with phenyl bromide in the presence of potassium carbonate to form 3-phenoxyphenyl ethyl ketone and then reacting this ketone with trimethylorthoformate to form the ketal. The ketal of 2-fluoro-4-biphenylyl ethyl ketone is formed by reacting 2-fluoro-4-biphenylyl ethyl ketone with trimethylorthoformate to form the ketal. The 2-fluoro-4-biphenylyl ethyl ketone can be prepared from 4-bromopropiophenone via 4'-bromo-3'-nitropropiophenone (see *Chemical Abstracts*, 61, p. 8232g), 4-propionyl-2-nitrobiphenyl (Ullman reaction), 4-propionyl-2-aminobiphenyl (reduction) and finally the Schiemann Reaction. See U.S. Pat. No. 3,793,457, Example 1 for a similar synthesis of 2-fluoro-4-biphenyl methyl ketone. The difluorobiphenyl ketone can be prepared by reacting 4-cyano-2,2'-difluorobiphenyl with ethyl magnesium bromide to form the di-fluoro biphenylyl ethyl ketone. See U.S. Pat. No. 3,755,427. This ketone can be converted to the ketal by the procedure described above.

When the reaction is conducted with the ketal starting material, the reactants are combined under as anhydrous conditions as is reasonably possible to maximize yields by minimizing the hydrolysis of the ketal to the ketone prior to enol ether formation. For example, the reaction vessel can be dried, purified with nitrogen to remove moisture laden air, and then filled with the trivalent thallium salt, organic solvent and ketal. The resulting mixture can be stirred or otherwise agitated and warmed to the optimum temperature range for that set of reactants and solvent mixture.

The above reaction of enol ethers will proceed in a variety of organic solvents and solvent mixtures, e.g., in $C_5$ to $C_7$-aliphatic and cycloaliphatic hydrocarbons, e.g., pentane, hexane, heptane, cyclohexane, cycloheptane, $C_1$ to $C_6$-alkanols such as methanol, ethanol, n-butanol, hexanol, ethers such as tetrahydrofuran, dioxane, lower saturated aliphatic nitriles such as acetonitrile, propionitrile, lower halogenated hydrocarbons such as methylene chloride, chloroform, ethylene dichloride and the like, and well as in commercially available solvent mixtures such mixed hexanes sold under tradename designations such as Skellysolve ® and the like, and mixtures of these solvents. Aromatic solvents such as benzene, toluene, xylene may also be used. The above solvents work best when TTN is used. When trivalent thallium sulfate is used a $C_1$ to $C_3$-alkanol, preferably methanol is used as the solvent for high yields of ester product, although solvent systems as different as benzene and methanol/sulfuric acid/trimethylorthoformate can also be used. A preferred embodiment of the invention when trivalent thallium sulfate is used is to react the enol ether with the trivalent thallium sulfate in an alcohol solvent such as methanol at a pH of 2 to 7, preferably pH 4 to 5.

When relatively stringently anhydrous conditions are to be maintained, e.g., as when the ketal or ketone is present in the mixture, water scavenger compounds such as tris($C_1$ to $C_3$-alkyl) orthoalkanoates e.g., trimethylorthoformate or tetra($C_1$ to $C_3$-alkyl)orthosilicates e.g., tetraethylorthosilicate should be included in the reaction mixture. When trivalent thallium halide and similar salts are used the reaction mixture should contain a water scavenger such as trimethylorthoformate for best results regardless which solvent system is used.

When the reaction is completed or has proceeded to the optimum degree, the mixture can be allowed to stabilize to room temperature and the ester intermediate product recovered from the reaction mixture by conventional procedures. For example, precipitated materials including the monovalent thallium salt by-product can be separated by filtration, the precipitate can be washed with solvent to remove therefrom any adhering product, and the washings and filtrate can be washed with water and inorganic salt in water solutions such as saturated sodium chloride solution to remove any water soluble constituents. The organic and aqueous phase can be separated and the organic phase dried by conventional means, e.g., over sodium sulfate. Removal of the organic solvent from the product ester can be accomplished by vacuum distillation of the solvent which leaves the ester as a residue, usually as an oil, which oil can be further purified by conventional means or the residue can be treated directly to convert the ester to the corresponding 2-aryl-$C_3$ to $C_6$-alkanoic acid product.

The ester intermediate product can be hydrolyzed or otherwise converted to the corresponding acid by conventional means. For example, the ester can be heated under reflux with a mixed aqueous/alcoholic solution of alkali metal hydroxide until the acid is formed, say for 0.5 to 3 hours. On cooling, the reaction mixture can be treated to recover the acid product, e.g., by washing the hydrolyzed reaction mixture with water, extracting with hexane to remove organic solubles, and the aqueous phase acidified with acid, and extracted with hexane. The extracts containing the acid product can be washed with aqueous salt solutions and dried. Thereafter, removal of the solvent by vacuum distillation leaves a crystalline acid product or an oil which crystallizes upon standing.

The invention is further described and exemplified by the detailed examples which follow but they are not intended to limit the scope of the invention.

EXAMPLE 1

In a dry round bottom flask there was placed under a nitrogen atmosphere 540 mg. (1.11 millimole) of anhydrous trivalent thallium nitrate (TTN*) and 5 ml. of dry hexane. To this mixture there was added 250 mg. (1.06 millimole) of a ketal of the formula

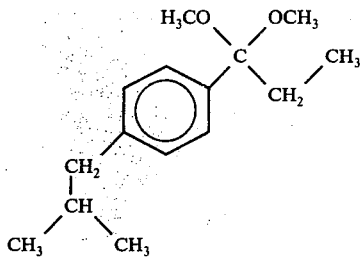

The resulting mixture was placed in a 55° C. oil bath and stirred for 2.5 hours. Analysis by gas liquid chromatography (glc) indicated the reaction was completed after about 1.5 hours. The mixture was cooled to room temperature, and the monovalent thallium nitrate by-product was removed by filtration and washed with hexane. The filtrate was washed with water and saturated sodium chloride solution before drying over sodium sulfate. Removal of the solvent in vacuo gave about 220 mg. (theory 233 mg.) of a pale yellow oil which was shown by nuclear magnetic resonance (NMR) and gas liquid chromatography (glc) to be greater than 90 percent methyl 2-(4-isobutylphenyl)propionate, compared to a known standard sample of the same compound.

* The anhydrous TTN can be prepaed by dissolving 7.89 gm. (18 millimoles) of trivalent thallium nitrate trihydrate in 7 ml. of absolute methanol and 7 ml. of trimethylorthoformate. After allowing the mixture to stand for about 1 hour the solvents are removed under vacuum to give about 8.40 gm. of a colorless viscous oil which is stored under nitrogen and used as $Tl(NO_3)_3 \cdot 3CH_3OH$.

Similar results were obtained when the process was conducted in methanol.

Alternatively, the anhydrous reagent can be generated in situ as described in Example 2.

EXAMPLE 2

To a solution of 379 mg. (3.71 millimoles) of trimethylorthoformate in 3 ml. of absolute methanol there was added 500 mg. (1.13 millimoles) of thallium trinitrate.trihydrate. After stirring the mixture for 30 minutes at room temperature, a solution of 240 mg. (1.02 millimoles) of ketal of the formula

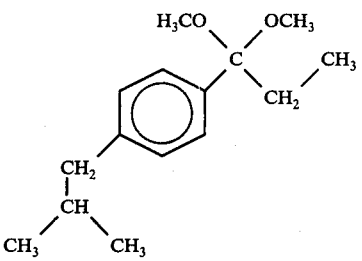

in 1 ml. of absolute methanol was added. The resulting mixture was heated at 55° C. for about 1.25 hr. Gas liquid chromatographic (glc) analysis indicated that the resulting mixture contained less than 2 percent starting material and about 94 percent of the methyl 2-(4-isobutylphenyl)propionate.

About 5 drops (excess) of 1-hexene was added to decompose excess thallium trinitrate and then on cooling the mixture, the resulting monovalent thallium nitrate was removed by filtration. The filtrate was concentrated in vacuo to give crude methyl 2-(4-isobutylphenyl)propionate as a yellow oil which was immediately hydrolysed by heating under reflux with 300 mg.

(3.75 millimoles) of 50 percent aqueous sodium hydroxide in 3 ml. of methanol and 5 ml. hexane for 2 hours to form 2-(4-isobutylphenyl)propionic acid. On cooling, the reaction mixture was treated with 20 ml. portions of hexane. The remaining aqueous phase was acidified with 1 N hydrochloric acid solution and was extracted twice with 15 ml. portions of hexane. The hexane extracts were washed with saturated sodium chloride solution and dried over sodium sulfate. Removal of the hexane solvent in vacuo gave about 210 mg. (100% crude) of ibuprofen, 2-(4-isobutylphenyl)propionic acid, as a pale yellow oil, which crystallized on standing. Recrystallization from hexane gave 146 mg., about 70 percent of theory, of ibuprofen.

This in situ process can also be conducted in other hydrocarbon diluent mixtures such as heptane, octane, cyclohexane and the like.

The procedure can be even further simplified by in situ generation of both the ketal and the anhydrous thallium (II) nitrate as described in Example 3.

EXAMPLE 3

To a solution of 831 mg. (about 78 millimoles) of trimethylorthoformate in 5 ml. of absolute methanol there was added 533 mg. (1.5 millimoles) of thallium trinitrate trihydrate and 190 mg. (1.0 millimoles) of ketone of the formula

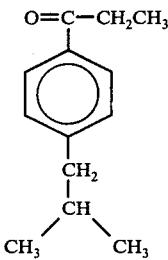

After stirring for 15 minutes at room temperature, the mixture was heated to reflux for about 15 minutes. Gas liquid chromatographic (glc) analysis indicated that the resulting mixture contained about 95% of the methyl 2-(4-isobutylphenyl)propionate.

Similar results were obtained with hydrated thallium (III) sulfate.

EXAMPLE 4

In a 10 ml. round bottomed flask there was placed 450 mg. (1.01 millimole) of thallium trinitrate trihydrate $(Tl(NO_3)_3.3H_2O)$ and 4 ml. of absolute methanol. The resulting solution was stirred at room temperature as 200 mg. (0.98 millimoles) of an enol ether of the formula

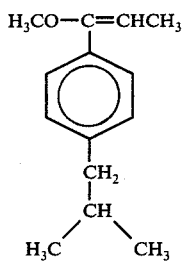

in 1.5 ml. of absolute methanol was added dropwise. An immediate exothermic reaction occurred and monovalent thallium nitrate ($TlNO_3$) precipitated. The mixture was stirred for 2.5 hours to insure complete reaction and the precipitate was removed by filtration. The filtrate was concentrated in vacuo and the residue was taken up in hexane. After washing the organic layer with saturated sodium chloride aqueous solution the organic layer was dried over sodium sulfate and concentrated in vacuo to give 210 mg. (theoretical yield in 216 mg.) of crude methyl 2-(4-isobutylphenyl)propionate. By NMR and glc analysis, this ester product was about 85–90 percent pure.

In a similar way, the reaction was carried out with thallium trinitrate trihydrate $[Tl(NO_3)_3.3H_2O]$ in tetrahydrofuran (THF), 10% THF/90% hexane, dioxane, and acetonitrile.

Equally good results were also obtained under similar conditions using anhydrous thallium trinitrate $[Tl(NO_3)_3.CH_3OH)]$ in THF, methanol, methylene dichloride and hexane.

EXAMPLE 5

To a solution of 3.4 gm. (8.92 millimoles) of commercially available thallium triacetate $[Tl(C_2H_3O_2)_3]$ in 25 ml. of absolute methanol stirred at room temperature under nitrogen in a 100 ml. round bottom flask there was added 1.74 gm. (8.53 millimoles) of crude enol ether of the formula

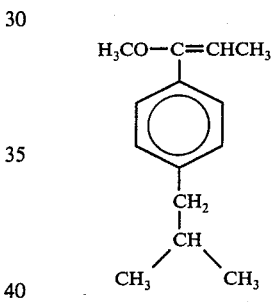

The resulting colorless solution was stirred for 24 hours, after which time glc analysis of a sample of the reaction mixture indicated that about 95 percent of the enol ether reacted. The resulting reaction mixture was concentrated in vacuo to give a yellow viscous oil which was triturated with hexane and filtered. The resulting hexane solution was washed with aqueous saturated sodium chloride solution and, after separation from the aqueous phase, the hexane solvent was removed in vacuo to give 1.9 gm. of methyl 2-(4-isobutylphenyl)propionate as a pale yellow oil. By glc analysis the oil was about 85 percent pure2-(4-isobutylphenyl)propionic acid (ibuprofen) methyl ester. NMR analysis of the oil confirmed that the ibuprofen methyl ester was the major product. The crude ester was hydrolyzed as described in the previous example to give 910 mg. of ibuprofen, after recrystallization.

EXAMPLE 6

To a solution of 50 ml. of absolute methanol stirred under nitrogen in an ice-salt bath (external temperature was about −5° C.) in a 100 ml. round bottom flask there was added 5.71 gm. (6.72 millimoles) of trivalent thallium sulfate heptahydrate $[Tl_2(SO_4)_3.7H_2O]$ followed in 1 minute by 1.37 gm. (6.72 millimoles) of crude enol ether of the formula

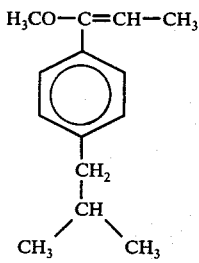

An immediate colorless precipitate was evident. The cooling bath was removed after 10 minutes and the mixture was stirred at room temperature for 2 hours, at which time glc analysis indicated about 90 percent conversion of starting enol ether had occurred. Approximately 1.5 ml. (about 12 millimoles) of 1-hexene was added to decompose the excess unreacted trivalent thallium salt. The solids were removed by filtration and were washed thoroughly with methanol. The filtrate and washings were concentrated in vacuo to give crude methyl 2-(4-isobutylphenyl)propionate as a pale yellow oil which was taken up in 50 ml. of hexane and washed with 25 ml. of saturated sodium sulfate in water solution. Removal of the hexane solvent from the organic phase gave methyl 2-(4-isobutylphenyl)propionate (about 87 percent pure by glc analysis). The ester was hydrolyzed as previously described to give, after recrystallization, 850 mg. of ibuprofen [(2-4-isobutylphenyl)propionic acid] in 61 percent overall yield.

In a similar manner, the ibuprofen can be obtained through its methyl ester by the reaction of the above enol ether with anhydrous trivalent thallium sulfate, $[Tl_2(SO_4)_3 \cdot _n CH_3OH]$.

EXAMPLE 7

To a cooled solution (ice-salt bath) of 50 ml. of absolute methanol stirred under nitrogen in a 250 ml. 3 necked round bottomed flask there was added 5.0 gm. (6.0 millimoles) of trivalent thallium sulfate heptahydrate $[Tl_2(SO_4)_3 \cdot 7H_2O]$. After 2 minutes, a solution of sodium methoxide in methanol (about 10 percent concentration) was added dropwise until the pH of the mixture had been adjusted to pH 4 to 5. With vigorous stirring 2.05 gm. (10.0 millimoles) of enol ether of the formula

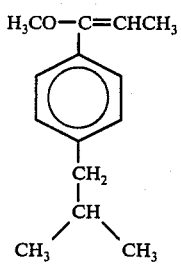

was added dropwise. The cooling bath was then removed and the mixture was stirred at room temperature. The pH was maintained between 3.5 and 4.5 by the addition of $NaOCH_3/CH_3OH$ solution as required. After 4 hours, glc analysis indicated that about 86 percent conversion to the methyl 2-(4-isobutylphenyl)propionate (ibuprofen methyl ester) had occurred. The mixture was stirred overnight at room temperature to complete the reaction. The mixture was concentrated in vacuo and the residue was partitioned between dilute sulfuric acid and hexane. The hexane layer was extracted with saturated sodium sulfate to give crude ibuprofen methyl ester. This ester was then hydrolyzed as previously described to give 1.33 g. (64 percent yield) of ibuprofen after recrystallization.

EXAMPLE 8

Following the procedure of Example 1 the ketal of the formula

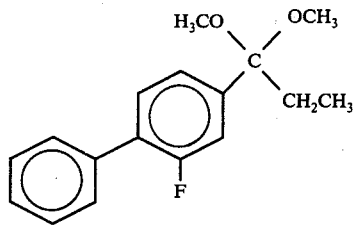

is reacted with TTN in dry hexane at 40° to 70° C. until methyl 2-(2-fluoro-4-biphenylyl)propionate is formed. This ester is then hydrolyzed to 2-(2-fluoro-4-biphenylyl)propionic acid (flurbiprofen) by the described procedure.

EXAMPLE 9

Following the procedure of Example 1 the ketal of the formula

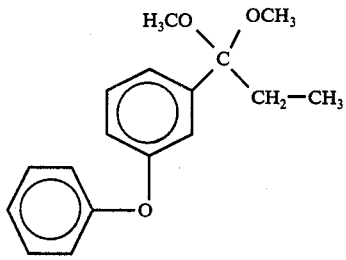

is reacted with TTN in dry hexane at 40° C. until methyl 2-(3-phenoxyphenyl)propionate is formed. This ester is then hydrolyzed to 2-(3-phenoxyphenyl)propionic (fenoprofen) acid by the described procedure.

EXAMPLE 10

Following the procedure of Example 3 the ketone of the formula

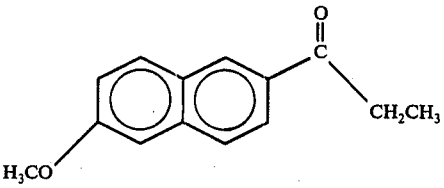

is reacted with TTN in dry methanol at reflux until methyl 2-(6-methoxy-2-naphthyl)propionate is formed. This ester is then hydrolyzed to 2-(6-methoxy-2-naphthyl)propionic acid (naproxen) by the described procedure.

EXAMPLE 11

Following the procedure of Example 4 the enol ether of the formula

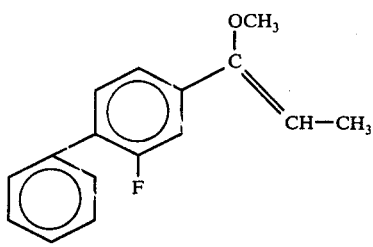

is reacted with trivalent thallium sulfate heptahydrate in methanol at about 0° C. until methyl 2-(2-fluoro-4-biphenylyl)propionate is formed. This ester is then hydrolyzed to 2-(2-fluoro-4-biphenyl)propionic acid by the procedure described above.

EXAMPLE 12

To a solution of 8.7 gm. (82 millimoles) of trimethylorthoformate there was added 11.1 gm. (25 millimoles) of thallium trinitrate trihydrate. After stirring this mixture for 30 minutes, 40 ml. of absolute methanol was added, followed by the addition of a solution of 4.5 gm. (about 23 millimoles) of a ketal of the formula

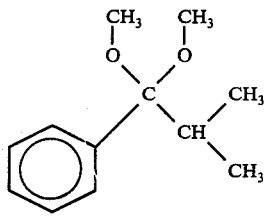

which ketal had been prepared from isobutyrophenone, trimethylorthoformate and a sulfonated polystyrene acid type resin (Amberlyst ® −15) in a few ml. of methanol. The resulting mixture was warmed in an oil bath at 60° C. for about 5 hours. Gas liquid chromatographic analysis indicated the resulting mixture contained greater than 90 percent of methyl 2-methyl-2-phenylpropionate.

This ester was hydrolyzed as described in the previous examples to give about 3.1 gm. (about 82 percent yield of crude 2-methyl-2-phenylpropionic acid as a colorless crystalline solid. This acid is a known compound which has uses as a plant growth regulator.

It is understood this process invention can also be applied to and includes the production of useful arylalkanoic acids having on the aryl ring carbon atoms thereof, any of the common, non-interferring substituents such as halogen, that is one or more fluorine, chlorine, bromine, or iodine atoms, a $C_1$ to $C_6$-alkoxy, e.g., methoxy, ethoxy, and/or nitro or acetamido groups and the like.

EXAMPLE 13

To a solution of 7.0 gm (66 mmol) of trimethylorthoformate in 25 ml. of absolute methanol was added 5.4 gm. (12 mmol) of thallium trinitrate trihydrate and 1.68 gm. (10 mmol) of ketone of the formula

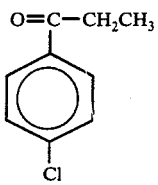

at 0°–5° C. The mixture was then heated to about 68° for approximately 5 hours. On cooling to room temperature the precipitated thallium nitrate was removed by filtration and the filtrate was concentrated in vacuo. The residue was taken up in hexane and the solution was washed with 3N aqueous $H_2SO_4$ solution. Removal of the solvent in vacuo gave crude methyl 2-(p-chlorophenyl)propionate. Hydrolysis of the ester as previously described hereinabove allowed isolation of 1.78 gm. (96%) 2-(p-chlorophenyl)propionic acid.

EXAMPLE 14

To a solution of 4.24 gm. (40 mmol.) of trimethylorthoformate in 25 ml. of absolute methanol is added 5.4 gm. (12 mmol) of thallium trinitrate trihydrate. The solution is stirred at 0°–5° C. as 2.17 gm. (10 mmol) of enol ether of the formula

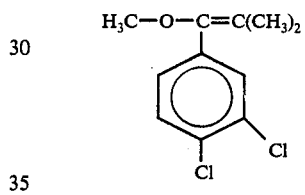

is added. The resulting mixture is heated at 60° C. until methyl 2-(3',4'-dichlorophenyl)-2-methylpropionate is formed. This ester is then hydrolyzed to 2-(3',4'-dichlorophenyl)-2-methylpropionic acid by the previously described procedure.

We claim:

1. A process which comprises reacting an enol ether of the formula

with trivalent thallium ions in an organic liquid containing at least one equivalent of an alcohol or water at a temperature of from about −25° C. to about reflux temperature of the mixture for a time sufficient to form a 2-aryl-$C_3$ to $C_6$-alkanoate ester of the formula

wherein in each formula

Ar is the aromatic moiety of a useful acid product containing from 6 to about 13 carbon atoms, in which the aryl ring portion of the aromatic moiety is a phenyl, phenoxyphenyl, naphthyl or biphenylyl group bonded to the carbon atom adjacent to the carboxyl ester moiety at an aryl ring carbon;

R is $C_1$ to $C_4$-alkyl, benzyl, phenyl, tris-($C_1$ to $C_3$-alkyl)silyl; and R' is equal to R or is an alkyl, benzyl, or phenyl group derived from the solvent medium;

Y and Z denote the residue of a $C_3$ to $C_6$-alkanoic acid moiety with each of Y and Z being hydrogen or $C_1$ to $C_4$-alkyl, with Y and Z having a total of from one to about 4 carbon atoms.

2. A process according to claim 1 wherein the enol ether (III) is prepared in situ from a ketal of the formula

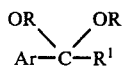  (II)

wherein Ar and R are as defined in claim 1 and $R^1$ is $-(CH_2)_nH$ where $n$ is 1 to 5 or $-CH(Y)Z$ wherein Y and Z are as defined in claim 1 under substantially anhydrous, acidic conditions.

3. A process according to claim 2 wherein the enol ether (III) and Ketal (II) are prepared in situ from a ketone of the formula

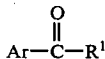

wherein Ar is as defined in claim 1 and $R^1$ is as defined in claim 2.

4. A process according to claim 1 wherein the trivalent thallium salt used is the nitrate, sulfate, perchlorate, fluoroborate, or acetate.

5. Process according to claim 1 wherein Ar is selected from the group consisting of phenyl, 3-phenoxyphenyl, $C_3$ to $C_5$-alkylphenyl, 4-biphenylyl, 4-biphenylyl substituted with up to 3 fluorine atoms on ring carbons thereof, and 2-naphthyl substituted in the 6-position thereof with methoxy;

R is $C_1$ to $C_4$-alkyl, benzyl, phenyl, or tris($C_1$ to $C_3$-alkyl)silyl. Y is $C_1$ to $C_4$-alkyl and Z is hydrogen.

6. Process according to claim 3 wherein Ar is $C_3$ to $C_5$-alkylphenyl,

R is $C_1$ to $C_4$-alkyl, Y is $C_1$ to $C_4$-alkyl and Z is hydrogen.

7. Process according to claim 6 wherein Ar is 4-isobutylphenyl, R is methyl, and Y is methyl and Z is hydrogen.

8. Process according to claim 5 wherein Ar is 3-phenoxyphenol,

R is $C_1$ to $C_4$-alkyl, Y is $C_1$ to $C_4$-alkyl and Z is hydrogen.

9. Process according to claim 8 wherein Ar is 3-phenoxyphenyl,

R is methyl, Y is methyl and Z is hydrogen.

10. Process according to claim 5 wherein Ar is 4-biphenylyl substituted with up to 3 fluorine atoms on ring carbons thereof, R is $C_1$ to $C_4$-alkyl, Y is $C_1$ to $C_4$-alkyl and Z is hydrogen.

11. Process according to claim 10 wherein Ar is 2-fluoro-4-biphenylyl,

R is methyl, Y is methyl and Z is hydrogen.

12. Process according to claim 5 wherein Ar is 2-naphthyl substituted in the 6-position with methoxy;

R is $C_1$ to $C_4$-alkyl; Y is $C_1$ to $C_4$-alkyl and Z is hydrogen.

13. Process according to claim 12 wherein Ar is 2-naphthyl substituted in the 6-position with methoxy, R is methyl, Y is methyl, and Z is hydrogen.

14. Process according to claim 5 wherein Ar is phenyl, R is $C_1$ to $C_4$-alkyl, Y and Z are each alkyl such that Y and Z together have a total of up to 4 carbon atoms.

15. Process according to claim 14 wherein Ar is phenyl, R is methyl, and each of Y and Z is methyl.

16. A process as defined in claim 1 which further includes the step of reacting the ester product (I) with a hydrolyzing acid or base to form an acid of the formula

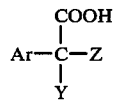

wherein Ar, Y and Z are as defined in claim 1.

17. A process as defined in claim 5 which further includes the step of reacting the ester product with a hydrolyzing acid or base to form an acid of the formula

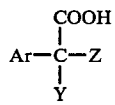

wherein Ar is 3-phenoxyphenyl, $C_3$ to $C_5$-alkylphenyl, 4-biphenylyl, 4-biphenylyl substituted with up to 3 fluorine atoms on the ring carbon atoms thereof or 2-naphthyl substituted in the 6-position with methoxy and Y and Z are hydrogen or $C_1$ to $C_4$-alkyl with Y and Z having a total of from 1 to 4 carbon atoms.

18. A process according to claim 1 wherein the enol ether (III) is reacted with thallium (III) sulfate in an $C_1$ to $C_3$-alkanol solvent at a pH of 2-7.

* * * * *